United States Patent
Hanna, Jr.

(10) Patent No.: US 11,351,235 B2
(45) Date of Patent: Jun. 7, 2022

(54) AUTOLOGOUS TUMOR VACCINES AND METHODS

(71) Applicant: Vaccinogen, Inc., Frederick, MD (US)

(72) Inventor: Michael G. Hanna, Jr., Seneca, MD (US)

(*) Notice: Subject to any disclaimer, the term of this patent is extended or adjusted under 35 U.S.C. 154(b) by 0 days.

(21) Appl. No.: 15/439,201

(22) Filed: Feb. 22, 2017

(65) Prior Publication Data

US 2018/0008686 A1 Jan. 11, 2018

Related U.S. Application Data

(63) Continuation of application No. 14/496,855, filed on Sep. 25, 2014, now abandoned.

(60) Provisional application No. 61/883,501, filed on Sep. 27, 2013.

(51) Int. Cl.
| | |
|---|---|
| *A61K 35/13* | (2015.01) |
| *A61K 45/06* | (2006.01) |
| *A61P 35/00* | (2006.01) |
| *A61K 39/00* | (2006.01) |
| *A61K 41/17* | (2020.01) |

(52) U.S. Cl.
CPC .......... *A61K 39/0011* (2013.01); *A61K 35/13* (2013.01); *A61K 41/17* (2020.01); *A61K 45/06* (2013.01); *A61K 2039/5152* (2013.01); *A61K 2039/572* (2013.01); *A61K 2039/80* (2018.08)

(58) Field of Classification Search
CPC .... A61K 39/0011; A61K 35/13; A61K 45/06; A61K 2039/5152; A61K 2039/572; A61P 35/00
USPC ...................................................... 424/277.1
See application file for complete search history.

(56) References Cited

U.S. PATENT DOCUMENTS

2003/0228300 A1* 12/2003 Haspel ............... A61K 39/0011
424/94.63

OTHER PUBLICATIONS

Peters et al. (Cancer Research, Apr. 1979, 39: 1353-1360).*

* cited by examiner

*Primary Examiner* — Yan Xiao
(74) *Attorney, Agent, or Firm* — Luedeka Neely Group, P.C.; Rick Barnes

(57) ABSTRACT

Autologous anti-cancer vaccines and methods of manufacture and treatment are provided, including expansion of individual patient-derived tumor cells in an immune-compromised animal(s) to attain, quantitatively and qualitatively, sufficient material for efficacious vaccine production and utilization, to elicit an immune response against micrometastases and/or recurrence in the individual patient following tumor excision.

11 Claims, No Drawings

AUTOLOGOUS TUMOR VACCINES AND METHODS

PRIORITY CLAIM

This application claims priority from U.S. Provisional Patent Application Ser. No. 61/883,501 filed Sep. 27, 2013, the disclosure of which is incorporated herein in its entirety.

FILED OF THE INVENTION

The present invention relates to autologous cancer vaccines and methods for generating and utilizing injectable vaccine doses containing immunogenic, and metabolically-active, but non-tumorigenic, cells for personalized therapy.

BACKGROUND OF THE INVENTION

A 2007 review by Finke et al., Vaccine 2007; 25 (Suppl 2):B97-109; PMID:17916465, distinguished active immunotherapy "cancer vaccines" as a separate entity from passive immunotherapy, which employs immune stimulatory agents or monoclonal antibodies. This analysis indicated that it is important to use the intended study population to assess the proportion of tumors that express the target of choice and the proportion of cells within each tumor that express it. The authors were focused on appropriate antigen discovery with the idea that meaningful commonalities can be found within and between different tumors, i.e., that inter-and intra-tumor antigenic homogeneity can be characterized and exploited.

Wood et al., "The Genomic Landscapes of Human Breast and Colorectal Cancers," Science 2007, asked the question: "how many genes are mutated in a human tumor"? To address this question, the authors analyzed the sequences of 20,857 transcripts from 18,191 human genes. In a typical breast or colorectal cancer, there are ~80 DNA mutations which result in amino acid alterations. Regardless of function, these mutated proteins all represent candidates for tumor-specific antigens, as they signify a meaningful difference from an individual's genetic blueprint which the immune system previously learned as "self." Although the number of mutant genes in breast and colorectal cancers was similar, the specific genes and types of mutations were quite different. Of the roughly 80 mutations in an individual tumor, only about three of these were common or meaningfully represented among a given population of tumors. Even more importantly, the probability these three mutations are found coincident in a significant number of tumors is exceedingly low.

Consequently, a highly effective prophylactic or therapeutic immune response against malignant disease requires an adaptable system. This is not likely to be achievable with pre-engineered allogeneic cells or any system reliant on a handful of "off-the-shelf" common antigens. Compositions and treatment methods capable of addressing the magnitude of cancer diversity are needed.

While the sequencing technology that uncovered these results is relatively new, phenomenological data has long demonstrated that tumor heterogeneity has been a significant impediment to treatment. In 1977, Fidler et al., Science, 197:4306 893-895, reported the discovery of phenotypic heterogeneity in transplanted tumors. Clones derived in vitro from a parent culture of malignant melanoma cells varied greatly in their ability to produce metastatic colonies in the lungs of syngeneic mice.

In the interim, investigations by the present inventor and colleagues (Hanna M G Jr, et al., Cancer Res 38:204 (1978); Hanna M. G. Jr., et al., Immunotherapy of Human Cancer, Raven Press (1978), pp 11-129; Hanna M. G. Jr. et al., Immunobiology and Immunotherapy of Cancer, W. D. Terry, Y. Yamamura, eds., Elsevier/North Holland (1979), pp 331-350; and Hanna M. G. Jr., et al., Cancer Immunol Immunother, 7:165 (1979)), have determined that the innate immune system has the adaptive potential to embrace and combat tumor heterogeneity, with certain restrictions. These studies, executed in L10 guinea pigs, demonstrated that the immune system can be educated to control systemic tumor burden after surgical excision of solid tumors.

The immune system constantly protects against an array of deadly foreign pathogens, viruses, and proteins. There is little doubt that vaccination against infectious disease represents one of the most important advancements in modern medicine. Yet, this success required advancements in technology which trained the immune system in a very specific manner. The most effective vaccines target infectious agents which are stable and rarely demonstrate antigenic change over time. Thus, a single product can be designed and widely deployed which addresses the full magnitude of the given disease. To the contrary, influenza, hepatitis C, HIV, and cancer represent more difficult challenges because they are highly adaptable entities which have resisted similar monotherapies.

Autologous cancer vaccines represent the next evolution of immunological training to combat malignant disease. However, a major impediment to progress in this realm is a lack of sufficient vaccination material to elicit an appropriate anti-tumor response. For many cancers, a patient's primary tumor is often too small to provide a sufficient number of cells to create a vaccine capable of generating an effective immunotherapeutic response.

Cancer vaccines have largely been utilized to treat advanced, disseminated disease. We now understand advanced tumors have the ability to evade immune detection by creating immunosuppressive environments. Immune effector cells are frequently found in advanced tumors; however, they exhibit an "exhausted" phenotype and are not functional. Consequently, the majority of cancer vaccines utilizing homogenous tools to treat advanced disease have failed in clinical trials. A more effective approach is to target the minimal residual disease left after surgery to eradicate the cells left behind, which would otherwise continue to grow and ultimately kill the patient.

Micrometastases, or tumor cell seeding, are extremely small collections of cancer cells which are often responsible for disease recurrence. Unfortunately, these cells are not detectable during surgery by conventional methods. These lesions are detectable by molecular techniques, such as polymerase chain reaction (PCR), and have been discovered in the regional lymph nodes of 54% of stage II colon cancer patients. Follow-up analyses have determined patients without PCR-detectable metastases have an adjusted 5-year survival of 91%, while 50% of the patients with micrometastases will die within the same time period (p=0.02). This is a significant public health issue that needs to be addressed.

The first autologous colon cancer vaccine used to prevent recurrence after surgical resection was OncoVAX®. Approximately 25% to 35% of patients diagnosed with Stage II (T3, T4 A & B) colon cancer will recur with disseminated disease, despite aggressive surgical resection. Adjuvant treatments with chemotherapeutic drugs have not demonstrated significant therapeutic benefit in these patients. This patient-specific vaccine is currently being evaluated in a Phase III trial granted Special Protocol Assessment and Fast Track designation by the FDA. OncoVAX® is an autologous vaccine using the patient's live, metabolically-active tumor cells to mobilize the body's immune system for the prevention of colon cancer recurrence following surgery. After a four injection protocol (two with the adjuvant TICE-BCG and two without), the risk of recurrence in stage II colon cancer patients drops from one in three to one in ten. Vermorken et al., Lancet, 353(9150), 1999.

Patient-specific vaccines are a significant improvement with respect to standard chemotherapeutic and radiation modalities. The cytotoxic agents used in modern chemotherapeutic protocols do not actively distinguish between normal and cancerous cells. Such methods rely on the inherent sensitivity of rapidly dividing cells to DNA-cross-linking and microtubule-arresting mechanisms. However, rapidly dividing normal cells are critical for multicellular life and arresting these processes leads to immunosuppression and other debilitating sequelae. Even so-called targeted agents (bevacizumab, cetuximab, etc) inhibit oncogenic pathways that also are utilized for normal homeostasis. In either instance, the current hope is the oncologist will deliver enough poison to kill the tumor before killing the patient. In contrast, autologous cancer vaccines can exert targeted effects by eliciting a specific immune response directed exclusively against the tumor-associated antigens on cancer cells. In the most recent phase III trial evaluating OncoVAX®, serious adverse events requiring BCG treatment cessation were extremely rare (8/128, 6%). Vermorken et al., Lancet, 353(9150), 1999. Additionally, once tumor-specific immunity is achieved, immunological memory protects the patient through constant surveillance; a mechanism not afforded by chemotherapeutic agents. Follow-up studies of OncoVAX® by Weger de V A, et al., Clin Cancer Res (Feb. 1, 2012) have demonstrated that OncoVAX®-treated patients still had improved recurrence-free survival compared to controls 15 years after initial treatment.

Large, early-stage, easily accessible tumors are a unique feature of colorectal disease. What is needed are methods for generating, quantitatively and qualitatively, sufficient tumor material to prepare autologous vaccine compositions, and associated advancements in cancer immunological treatment, for all carcinomas, including patients with solid tumors too small for preparing efficacious vaccines according to previously known methods.

BRIEF SUMMARY OF THE INVENTION

The present disclosure provides significant advancements in patient care and cancer mortality. During the initial trials evaluating OncoVAX®, we have determined that at least about 3.5 grams of tumor was required to create the four sequential doses for an effective immune response against minimal residual disease. Unfortunately, when most cancers (melanoma, breast, etc) have progressed to 3.5 grams, tumor burden is often systemic, immunosuppressive, and consequently not susceptible to previous treatment modalities.

In addition, previous studies significantly underestimated the degree of intra- and inter-tumor heterogeneity which hampered antigen discovery for cancer vaccine development. By treating cancer as a homogeneous disease, cancer immunologists have not adequately trained a patient's immune system to recognize the abundant foreign or "nonself" components of an individual's unique tumor. The present invention enhances autologous cancer vaccine technology by further embracing tumor heterogeneity and extending this technology to other types of cancer, notably solid tumors of relatively small size which would otherwise limit their utility to generate sufficient material for a meaningful therapeutic response as an autologous vaccine or related method of treatment.

We have found that an effective immune response against minimal residual disease and recurrence after surgery, particularly in stage II/III colon cancer, typically requires at least two, three, preferably four or more injectable doses of autologous non-tumorigenic cells. Additionally, each dose should ideally contain at least 0.7 to $1.3 \times 10^7$ tumor cells administered during an immunotherapeutic treatment regimen. Heretofore, this has placed a physical restriction on the types of cancer patients who could be treated with an efficacious autologous cancer vaccine. Based on new techniques discussed herein, patient-derived primary tumors of relatively small size (<3.5 grams) can now be expanded in a manner that provides sufficient material for an effective immunogenic response, while simultaneously preserving the heterogeneity of the source lesion.

One aspect the present invention provides methods for making an injectable, autologous, anti-neoplastic vaccine containing at least about $10^7$ viable, non-tumorigenic tumor cells, by excising a solid tumor from a cancer patient to obtain at least 95% of the patient's solid tumor tissue, wherein the excised tumor tissue has a weight of less than about 3.5 grams; digesting the excised tumor tissue to obtain dissociated tumor cells; transplanting the excised tumor cells into an immune-compromised animal; propagating the tumor cells in the animal to obtain expanded tumor tissue; harvesting the expanded tumor tissue from the animal to obtain harvested tumor cells, wherein the harvested tumor tissue (alone or from multiple transplants) has a weight of at least about 3.5 grams; applying a dose of gamma radiation to the harvested tumor cells to render the cells non-tumorigenic; and combining the non-tumorigenic cells with a pharmaceutically acceptable carrier for injection to prepare an injectable dose containing at least about $10^7$ tumor cells. In one aspect, the expanded cells have at least 85% sequence homology to the tumor cells of the patient's solid tumor. In another aspect, the injectable dose comprises tumor cells having at least 80% viability.

The method in another case comprises digesting the excised tumor tissue with an enzyme or combination of enzymes to obtain dissociated tumor cells and mixing the dissociated tumor cells to form a homogeneous suspension. The method of manufacture additionally may comprise digesting the harvested tumor tissue to obtain dissociated harvested tumor cells and mixing the dissociated harvested tumor cells to form a homogeneous suspension.

In one aspect, the tumor cells transplanted into the animal comprise 95-100% by weight of the patient's solid tumor. In another aspect, the tumor cells harvested from the animal comprise 95-100% by weight of the expanded tumor tissue.

The method of autologous vaccine manufacture may further comprise transplanting the harvested tumor tissue into a second immune-compromised animal, propagating the tumor tissue in the second animal, and harvesting the propagated tumor tissue from the second animal to prepare the injectable dose containing at least about $10^7$ tumor cells.

In one aspect, the animal is a rat. In another, the animal is an athymic nude mouse that optimally has received treatment to reduce Natural Killer Cell activity or has Severe Combined Immunodeficiency Disease (SCID). In another aspect, the transplanted tissue is harvested when it has a weight of about 3.5 to 4 g.

The method of autologous vaccine manufacture may further comprise treatment of the harvested tumor, before dissociation, with a disinfectant solution at a concentration and for a duration that provides anti-microbial activity while minimizing cytotoxicity. In another aspect, the method includes characterizing the antigenic profile of the harvested cells via DNA or RNA sequencing, flow cytometric analysis, or proteomic analysis to ensure that the heterogeneity of the patient's tumor has been preserved.

In yet another aspect, the method further comprises applying a dose of gamma radiation to the harvested cells in an amount sufficient to inactivate microorganisms, eliminate tumorigenicity, and preserve the viability of the cells to obtain sterile, non-tumorigenic, and immunogenic tumor cells.

The present invention further provides methods for eliciting an immune response to prevent the recurrence of metastases in a cancer patient in need, comprising: excising a solid tumor from a cancer patient to obtain at least 95% of the patient's solid tumor tissue, wherein the excised tumor tissue has a weight of less than about 3.5 grams; digesting the excised tumor tissue to obtain dissociated tumor cells; transplanting the tumor cells into an immune-compromised animal; propagating the tumor cells in the animal to obtain expanded tumor tissue; harvesting the expanded tumor tissue from the animal, wherein the harvested tumor tissue has a weight of at least about 3.5 grams; applying a dose of gamma radiation to the harvested tumor cells to render the cells non-tumorigenic; combining the non-tumorigenic tumor cells with a pharmaceutically acceptable carrier for injection to prepare an injectable dose containing at least about $10^7$ tumor cells having at least 85% sequence homology to the cells of the patient's tumor; and administering to the patient said injectable dose to elicit an immunogenic response against recurrence of said cancer.

In another aspect, the method for eliciting an immune response further comprises combining the harvested tumor cells with a pharmaceutically acceptable carrier for injection to prepare at least four injectable doses each containing at least about $10^7$ dissociated tumor cells having at least 85% sequence homology to the patient's excised tumor; and administering each of the at least four doses in a treatment regimen sufficient to elicit an immune response against recurrence of said cancer. In a preferred aspect, the harvested tumor cells have at least 95% sequence homology to the cells of the patient's tumor.

In another aspect, the treatment method further comprises administering an adjuvant or immune stimulator with one or more of the doses.

In one aspect of the method for eliciting an immune response, the tumor transplanted into the animal comprises 95-100% by weight of the excised solid tumor and the harvested tumor tissue comprises 95-100% by weight of the expanded tumor tissue.

In another aspect, the method for eliciting an immune response further comprises applying a dose of about 150,000-200,000 rads of gamma radiation to the tumor cells to render the tumor cells sterile and non-tumorigenic.

In one aspect, the patient in need has stage III or earlier cancer. In another, the patient in need has stage II or earlier cancer. In certain aspects of the invention, the patient has cancer selected from the group consisting of colon, renal, melanoma; cervical, ovarian, prostate, pancreatic, or breast cancer, or any solid tumor subtype.

In a particular aspect, the patient has colon cancer and tissue excising is performed during colonoscopy. In a further aspect, the method includes washing the excised tumor tissue with a solution containing a detergent; treating the excised tumor tissue with a disinfectant to reduce microbial contamination of the tissue; and digesting the tumor tissue with a dissociation enzyme(s), in the presence of at least one antibiotic and an anti-mycotic, to obtain at least about $10^7$ dissociated tumor cells.

In addition, the present invention further provides whole cell autologous anti-cancer vaccine compositions for administration to a patient after surgery to excise a solid tumor having a weight less than about 3.5 g, the composition comprising: at least about $10^7$ viable non-tumorigenic tumor cells having at least 85% sequence homology to the cells of the excised tumor; and a pharmaceutically acceptable carrier for injection; wherein the composition gives rise to an immunogenic response when administered via intradermal injection to the patient. In another aspect, the composition comprises at least four doses each containing at least about $10^7$ viable non-tumorigenic tumor cells having at least 85% sequence homology to the cells of the excised tumor. In yet another aspect, the vaccine comprises at least $10^8$ viable non-tumorigenic tumor cells having at least 85% sequence homology to the cells of the excised tumor. In preferred aspects, the tumor cells of the vaccine have at least 95% sequence homology to the patient's primary tumor cells and are sterile, non-tumorigenic, and at least 80% viable.

The present invention also provides methods for making an injectable autologous anti-neoplastic vaccine containing at least about $10^7$ viable, non-tumorigenic tumor cells, comprising (without xenografting): excising a solid tumor from a cancer patient to obtain at least 95% of the patient's solid tumor tissue, wherein the excised tumor tissue has a weight of greater than 3.5 grams; digesting all of the excised tumor tissue with an enzyme(s) to obtain dissociated tumor cells; mixing the dissociated tumor cells to prepare a homogeneous suspension of heterogeneous cells, wherein any aliquot of the suspension contains a full complement of antigenic material from the patient's solid tumor; applying a dose of gamma radiation to the homogeneous suspension of tumor cells to render the cells non-tumorigenic; and combining the non-tumorigenic tumor cells with a pharmaceutically acceptable carrier for injection to prepare an injectable dose containing at least about $10^7$ tumor cells. In another aspect, non-tumorigenic cells in each dose have at least 98% sequence homology to the patient's tumor cells. In another aspect, the method further comprises characterizing the antigenic profile of the cells to ensure original tumor heterogeneity has been preserved.

According to a further aspect, the method for making an injectable autologous anti-neoplastic vaccine (without xenografting) comprises applying a dose of gamma radiation to the cells in an amount sufficient to inactivate microorganisms and tumorigenicity and preserve the viability of the cells, to obtain sterile, non-tumorigenic, and immunogenic tumor cells.

DETAILED DESCRIPTION OF THE INVENTION

Each vaccine according to the present disclosure is constructed from a patient's own primary tumor and effectively addresses the genetic diversity or heterogeneity of malignant solid tumors. Consequently, the supervised antigen discovery process typically employed for developing effective cancer vaccines is handled in an unsupervised manner by the patient's own immune system, which ultimately provides a robust anti-tumor response.

Patients in need include any animal or human that has undergone or will undergo surgery for removal of a solid tumor. The techniques discussed herein are particularly useful where the solid tumor has a relatively small size, such as about less than about 3.0 to 3.5 grams. After surgical excision, the potential for micrometastases and/or recurrence is prevented following administration of the autologous vaccines as disclosed herein. The present techniques are applicable against all types of cancers, including carcinomas of epithelial origin, as well as solid neurological tumors, and cancers of endothelial or mesothelial origin, preferably of stage III or earlier disease. The vaccine compositions and methods herein may also be combined with immune check point inhibitors or chemotherapeutic standard of care pharmaceuticals, particularly for treating more advanced malignant disease (stage III/IV).

Autologous tumor vaccines and, specifically, OncoVAX® therapy, are designed to activate a patient's defenses against tumor-associated antigens and can further enhance the immunogenicity of autologous tumor cells. OncoVAX is currently prepared individually for each patient for the adjuvant treatment of stage II and stage III colon carcinoma after surgical resection. The product contains two distinct biological entities: (1) viable, but non-tumorigenic, autologous cancer cells and (2) fresh-frozen, BCG bacteria. The first two vaccine doses contain $1.0 \times 10^7$ viable, metabolically-active, non-tumorigenic, sterile cancer cells, admixed with $1.0 \times 10^7$ colony forming units (CFU) of fresh-frozen BCG, in a final volume of 0.2 to 0.4 ml sterile Hanks' Balanced Salt Solution (HBSS). The subsequent two vaccine doses are prepared similarly, but without the addition of BCG. The present invention extends autologous tumor vaccines to cancer patients, including, but not limited to, colon, renal, melanoma, ovary, prostate, lung, and pancreatic cancer patients, who have tumors too small for previously known autologous cancer vaccine therapies.

Each dose of autologous vaccine according to one aspect of the present invention contains from at least about 0.7 to $1.3 \times 10^9$, at least 0.7 to $1.3 \times 10^8$, or at least 0.7 to $1.3 \times 10^7$ viable, metabolically-active, non-tumorigenic, tumor cells, each dose having at least about 85%, 90%, 95%, or 98 to 100%, sequence homology to the cells of the patient's primary tumor. In certain embodiments, at least three, four, five or more doses are administered over a treatment period. A booster dose may be administered in some aspects of the invention at a subsequent time, such as six months, after a sequence of initial injections, as discussed herein. By the presently disclosed methods, each such dose comprises a sufficient number of tumor cells and is phenotypically, genomically, and/or antigenically the same as or similar to any previous dose, as well as to the primary tumor, regardless of the size of the primary tumor.

Heretofore autologous vaccine manufacturing processes typically began with an approximate minimum of one cubic cm of primary tumor, or about 3.5 g of tumor cells, excised from the patient. Because tumors are heterogeneous and can differ in antigenicity, cellularity, and viability within tumors and across different patients, as much tumor tissue as is available should be collected for further processing to prepare homogeneous doses of heterogeneous cells. Preferably, all of the available tumor tissue is dissociated and blended or mixed into a homogeneous single-cell suspension to maintain all tumor antigens and cell types uniformly in all aliquots during manufacture. According to previous techniques, only primary tumors ≥about 3.5 g were used for vaccine preparation. If the weight of the collected tumor tissue was <about 3.5 g, the pathologist would, if possible, increase the quantity of tumor provided by obtaining additional portions of the excised primary tumor. However, if the tumor weighed significantly more than the necessary minimum of about 3.5 g, heterogeneity would not necessarily be preserved and resulting doses of autologous cells would lack some or all of the immunologically necessary antigens for a robust response.

Using the techniques of the present invention, primary tumors and tumor tissue quantities of any mass, including greater or less than 3.5 g, and as low as about 2.0, 1.0, 0.5, 0.1 g, or less can now be expanded and processed to prepare effective autologous vaccines for immunotherapeutic treatment.

In one aspect, the present invention thus provides methods for making and using OncoVAX® and numerous other autologous vaccines from patient primary tumors that are otherwise too small for effective vaccine doses and treatment regimens. Several common carcinomas were not previously amenable for processing into efficacious autologous vaccines due to the limited size of the tumor at diagnosis. These include, but are not limited to, renal, breast, pancreatic, prostate, cervical, ovarian, early stage malignant melanoma, and others, having a relatively small size, i.e., less than 3.5 grams (herein referred to as "small tumors"). In many cancers, a tumor of this size is sufficient for metastasis and potentially fatal recurrence, but is generally insufficient for processing to manufacture vaccine products for effective doses and treatment regimens, as discussed herein.

One aspect the present invention provides tumor cell compositions and autologous vaccines by transplanting and expanding a patient's tumor cells in immune-compromised animal hosts. Expansion of tumor cells without the usual immune selection processes of a typical host animal provides a means of expanding autologous vaccines such as the application of OncoVAX® technology to the majority of fatal carcinomas that produce solid tumors of less than 3.5 grams, while exploiting the genomic diversity of the autologous tumor to prevent recurrence via use of the autologous vaccine doses, either alone or in strategic combination with adjuvants or standard of care chemotherapy.

In one embodiment of the present invention, the patient-derived cells are dissociated and mixed in a suspension to create a homogeneous mixture of heterogeneous cells, such that any aliquot of the composition is representative of the other, and reflects the specific biological properties (phenotypic, genomic, or antigenic) of the primary tumor. Additionally, pre- and post-engraftment dissociation allows any aliquot of the suspension to be analyzed by any number of bio-analytic processes (including, but not limited to, species-specific PCR, microarray, RNA-seq, whole genome deep sequencing, flow cytometric analysis, etc) to establish the vaccine product has not experienced a shift in genomic or antigenic heterogeneity during propagation.

Thus, the vaccine products according to the present invention are typically prepared from excised solid tumors of less than 3.5 g, and the resulting vaccine products are available in a total mass of viable, non-tumorigenic, and preferably sterile tumor cells, which permit the preparation of individual doses, preferably at least four injectable doses, each containing at least about 0.7 to $1.3 \times 10^7$ viable, non-tumorigenic, and sterile tumor cells. Each dose may further contain any suitable adjuvants, or immune stimulators, such as any form or strain of BCG, or any suitable pharmaceutically acceptable carrier for injection.

In a particularly preferred embodiment, the autologous vaccine products contain two distinct biological entities: (1) viable autologous tumor cells propagated in an animal host from the patient's primary tumor tissue, and (2) fresh-frozen, BCG bacteria. The first, second, or subsequent vaccine doses may contain at least about $1.0\times10^7$ viable, metabolically-active, non-tumorigenic, sterile tumor cells admixed with, for example, $1.0\times10^7$ colony forming units (CFU) of fresh-frozen BCG, in a final volume of, for example, 0.2 to 0.4 ml sterile Hanks' Balanced Salt Solution (HBSS). The subsequent one, two, or more vaccine doses may be prepared similarly, but without the addition of BCG. The doses may be cryopreserved according to controlled rate freezing methods. In some embodiments, the prepared patient dose is drawn into a syringe labeled with appropriate patient information. The capped syringe is then packed in an insulated container and delivered to a location for intradermal administration of the vaccine to the patient. The vaccine is typically administered within 4 hours of thawing the cells, typically using a regimen of three weekly induction vaccinations and a six month booster, although any suitable dosage and treatment regimen may be utilized and may be determined by the patient care provider given the teachings herein.

The tumor cells are initially derived from the patient's own solid tumor, which has been surgically removed and processed to a single cell suspension, which may then be cryopreserved. Using a sterile scalpel, any large pieces of tumor tissue are cut into typically no smaller than 1.5 cm pieces to facilitate rapid cooling and nutrient availability during transport. Since the tumor tissue may be subjected to disinfection during the manufacturing process, cutting the tumor into smaller than 1 cm pieces is preferably avoided.

After excision, the tumor tissue may be digested with a dissociation enzyme(s), typically in the presence of at least one antibiotic and an anti-mycotic, to obtain dissociated tumor cells. Dissociation of the tumor may be performed in the presence of, for example, levofloxacin, amphotericin B, Primaxin (imipenem and cilastatin) and/orgetamicin sulfate to reduce endogenous bioburden, which is inherent to, for example, colon-derived tumors. Single cell suspensions of the dissociated tumor cells may be frozen and viably recovered for later use for expansion as xenografts according to the teachings herein. According to one aspect, any and all cells derived from the primary relatively small tumor are utilized for xenografting, excepting a sufficient aliquot (such as, for example, less than about 1-5% of the total cell suspension) of cells for RNA-seq or other methods of pre- and post-xenografting bio-analytical quality control, as discussed herein.

Severe combined immune deficient (SCID) mice animal hosts are utilized in one aspect of the present invention. Various other immune deficient mice, rats, rodents or other immune compromised animals also may be used, including those which are deficient as a result of a genetic defect, which may be naturally occurring or induced, such as, for example, nude mice, Rag 1 and/or Rag 2 mice, and mice which have been cross-bred with these mice. The deficiency may be, for example, as a result of a genetic defect in recombination, a genetically defective thymus, or a defective T-cell receptor region. Induced immune deficiency may be as a result of administration of an immunosuppressant, e.g., cyclosporin, removal of the thymus, or treatment to reduce NK activity, including, but not limited to, anti-asialo-GM1 antibody treatment. Various transgenic immune-deficient animals are currently available or can be developed in accordance with known techniques. Ideally, the immune-deficient animal is a rat or mouse having a defect which inhibits maturation of lymphocytes, particularly lacking the ability to rearrange the T-cell receptor region. In one embodiment, the animal host is the NSG, NOD SCID gamma (005557) mouse from The Jackson Laboratory, although any suitable immune-deficient or immune-compromised animal may be used.

Suitable immune-deficient animals include rodents, preferably rats and mice, including, but not limited to, NSG NOD SCID gamma, NOD SCID, BALB SCID, B6 Rag, Outbred Nude, and Inbred Nude, as available from The Jackson Laboratory, Bar Harbor, Me.; and Athymic Nude, BALB/c Nude, CD-1 Nude, Fox Chase SCID® Beige, Fox ChaseSCID®, NIH-III Nude, NMRI Nude, NOD SCID, NU/NU Nude, OT II Mouse, RNU Rat, and SHC™ Mouse, as available from Charles River Laboratories, Hollister, Calif.

Tumor xenografts from the digested and preferably homogeneous and uniform cell suspensions may be established in the immune-deficient animals by the implantation, such as subcutaneous implantation, of the dissociated cancer explants surgically removed from the patient, such as animals and human patients with stage II or stage III cancer or locally advanced or metastatic disease. The site of implantation of the tumor cells may be into any subcutaneous or other site which will permit blood supply to reach the xenograft, such as the flanks of the host animal. Tissue from primary tumors as well as from sites of lymph node, lung, bone, and other organ metastases may be used to establish the solid tumor xenografts.

Once established, the xenograft tumors propagate and provide enhanced source material by weight and volume for further use. The xenografts preferably retain the human phenotype as determined by, for example, human β-globin expression, express human cancer-specific antigens, and retain growth characteristics reflective of the primary tumor. This aspect of the invention provides methods for generating quantities of tumor cells for autologous vaccine manufacture. In one embodiment, a method for expanding small colon tumors from a colonoscopy patient involves subcutaneously implanting these cells in a dissociated suspension into a nude SCID or other immune-deficient animal and allowing the implanted material to grow as a xenograft to a sufficient number of cells for the preparation of an effective autologous vaccine to protect the patient from recurrence or additional colon lesions with a similar antigenic profile. The expanded human cancer cells are then obtained by harvesting the xenograft and digesting the cells for further processing, as discussed herein.

Subcutaneous tumors can grow quickly and the host animal is typically sacrificed within 2-6 weeks. Alternative methods which further increase the number of cancer cells are also provided, such as in the event that a first round of xenografting does not produce a sufficient quantity of tumor material by weight. The xenografts may be further expanded by serial propagation in additional immune-deficient animals, with sufficient samples stored for long-term evaluation of genomic, proteomic, or antigenic drift.

Single cell suspensions of xenograft tumor tissue may thus be used to seed additional immune-deficient animals via serial passage, and may be frozen and viably recovered for later use, such as for a therapeutic indication in the primary donor. Serial passage of xenograft tumors in additional animals may be used to obtain larger quantities of patient solid tumor cells that are phenotypically, antigenically and, moreover, immunologically, similar or identical to the primary tumor, and have at least 85% sequence homology to the genomic sequence of the primary tumor. The invention provides cancer xenografts which retain stable cancer cell phenotypes through multiple passages in nude SCID mice or other suitable immune-compromised animal hosts. Tissue harvested from xenograft tumors is used to prepare single cell suspensions of human or veterinary patient tumor cells. Single cell suspensions prepared from digested xenografts also retain the biological properties of the parental tumors. The single cell suspensions may be used to establish, for example, new subcutaneous tumors. Accordingly, methods of the invention include transplanting the harvested tumor tissue into at least a second immune-compromised animal, propagating the tumor tissue in the second animal, and harvesting the propagated tumor tissue from the second animal. The tumor cells may be passaged from 3 to 5, to 9, or even to 10 or more times in additional immune-compromised animals. In preferred embodiments, all of the propagated tumor tissue is harvested such that the subsequently prepared aliquots of single cell suspensions, for either passage into additional immune-compromised animals, or for vaccine product preparation or quality control tests, contain the full antigenic compliment of the patient's original tumor.

In one aspect of the invention, the original tumor cells transplanted into the host animals comprise about 95-100% by weight of the patient's solid tumor, preferably about 98-100% by weight, and the tumor cells harvested from the animals comprise about 95-100% by weight of the propagated tumor tissue, preferably about 98-100% by weight. In one embodiment, the respective transplant(s) and/or harvested material for vaccine manufacture comprise about 99% by weight of the existing tumor material, thus maintaining about 1% for quality control purposes. Each seeding or serial passage, and each collection of harvested expanded tumor cells, is preferably dissociated to a homogeneous single cell suspension of heterogeneous cells such that each aliquot and each injection or xenograft is representative of the heterogeneous nature of the primary tumor. In other words, the antigenic heterogeneity of the primary tumor is preferably preserved at each step of the process, so that the vaccine contains the full complement of antigens needed by the patient for the development of a robust immunogenic response against any micrometastases and/or recurrence. Accordingly the invention also provides methods for transplanting an aliquot of the combined harvested tumor cells into at least a plurality of immune-compromised animals, propagating the tumor tissue in the plurality of animals, and harvesting the propagated tumor tissue from the plurality of animals, wherein the tissue harvested from each animal, and also the vaccine products prepared therefrom, are immunologically similar or identical to the full complement of cells from the primary tumor.

In one aspect, the primary tumor cells are transplanted under the skin of the immune compromised animal. Transplanting of the tumor tissue may also be under the animal's kidney capsule, in the animal's peritoneal cavity, in the bone marrow, or any other suitable location to generate sufficient tumor material for autologous whole cell tumor vaccinate preparation using the expansion of patient tumors in immune-deficient animals.

After quantities of tumor cells are propagated as discussed herein, the xenografts are excised, dissociated, and used in the preparation of vaccine products and autologous whole cell vaccination. The harvested xenograft(s) may be washed with a physiological solution containing a detergent, and the harvested tumor may be washed with a disinfectant solution at a concentration and for a duration that provides anti-microbial activity while minimizing cytotoxicity to human cells, before being further digested and dissociated. The expanded tumor tissue is then typically digested with a dissociation enzyme(s), in the presence of at least one antibiotic and an anti-mycotic, to obtain a suspension of dissociated tumor cells for further processing.

The cell suspensions may then be subjected to a dose, such as of about 150,000-200,000 rads of gamma radiation to render the cells non-tumorigenic. Radiation is preferable, but may not necessarily be applied, while the cells are frozen. U.S. Pat. No. 5,484,596 ("the '596 patent") provides methods for treating human colon cancer patients with resectable solid tumors to inhibit recurrence and formation of metastases. The '596 patent refers to surgically removing colon tumor tissue from a human cancer patient, treating the tumor tissue to obtain tumor cells, irradiating the tumor cells to be viable but non-tumorigenic, preparing a vaccine composition comprising viable but non-tumorigenic tumor cells, and injecting the vaccine intradermally after the cancer patient's immune system has recovered from surgery. The same methods may be used to process the expanded tumor cells from harvested xenografts as taught herein, although such methods are not limited to colon tumors. The '596 patent is expressly incorporated by reference herein in its entirety.

By virtue of the origin of colon tumors within the large bowel, cancer vaccines produced by the process of the '596 patent are not sterile. To obtain an effective immunogenic cell preparation for vaccine purposes, the tumor cells should be viable and metabolically-active. Thus any treatment to render the cells sterile must not unduly compromise the essential biological characteristics of the intact, live cells required for immunization and clinical efficacy.

U.S. Pat. No. 7,628,996 ("the '996 patent") provides methods for achieving safe, sterile tumor cell compositions, without incurring substantial changes to the immunogenic properties of the tumor cells. These goals are not necessarily compatible, because while sterilization can inactivate microbial infection, it can also negatively impact mammalian cells; potent disinfectants are effective against microbes but, in sufficient doses, can also harm mammalian cells. Radiation can render microbes inactive, but excess radiation can also substantially modify the immunogenic and subsequent biological properties of mammalian cells.

The '996 patent refers to a combination of chemical and biological means for removing and inactivating bio-burden from tumor cells to obtain sterile cell compositions that remain viable and immunogenic for the production of therapeutic and prophylactic products. This sterilization treatment method is useful for a wide variety of cell types; however, it is considered to be particularly useful for sterilizing solid tumor tissue for the preparation of cancer vaccines, including, by way of example, the autologous colon cancer vaccine of the '596 patent. The '996 patent is expressly incorporated by reference herein in its entirety, The present invention further provides methods of treating cancer and preventing the recurrence of primary disease and/or metastases by administering one or multiple doses of a sterile vaccine containing sufficient quantities of viable, metabolically-active, but non-tumorigenic cancer cells derived from solid tumors, prepared by combining expanded tumor cells with a pharmaceutically acceptable carrier for injection to prepare injectable intradermal doses, each preferably containing at least about $10^7$ dissociated tumor cells having at least 80% viability as measured by Trypan Blue exclusion, and thus eliciting an immunogenic response when injected into the specific patient of interest, typically in a regimen of four, five, or six doses, optionally one or more of these including an immune adjuvant such as BCG, in amounts as illustrated herein.

The above and other aspects of the present invention are illustrated by the following non-limiting examples.

Example 1

Acquisition of Patient Primary Tumor Cells:

Pre-production involves the acquisition of the source material (tumors) for the manufacture of an autologous vaccine and, therefore, includes all of the handling of the tumor outside the vaccine production facility. This typically comprises the surgical tumor resection, the dissection, pathological processing, and transport of the tumor to the manufacturing facility. Operating room and pathology personnel should be trained in accordance with specific protocols concerning collection and tumor processing. After resection of the tumor-containing colon specimen, the resected colon is placed in a sterile bag or basin. The resected colon will be processed within the operating suite. The resected colon is cut open, and washed in accordance with the standard operating procedure. The pathologist performs the dissection of the tumor after which the tumor is prepared for transport to the production facility. For transport, the tumor may be put in a tumor transport bottle containing Hanks' Balanced Salt Solution containing gentamicin (HBSS/G). The tumor transport bottle may be packed in a transport box containing a temperature logging device and cold packs to ensure maintenance of the specified transport temperature.

During the production process, several acceptance criteria should preferably be met in order to continue processing. Minimum tumor weight (about 3.5 g) will determine whether the tumor processing is initiated without xenografting. If so, in order to obtain a vaccine containing the entire antigenic complement of the primary tumor, the entire tumor of greater than 3.5 g is collected and dissociated to prepare a homogeneous single cell suspension of heterogeneous cells. Acceptance criteria for the biological substance include number and viability of the tumor cells, as well as identity and potency of the tumor cells.

The tumor is washed using HBSS/G and transferred to a sterile dish in which the extraneous tissue from the tumor is removed and discarded. The tumor is then transferred into a bottle containing a disinfectant. After this treatment, the disinfectant fluid is removed and the tumor is washed with HBSS/G.

The tumor is then trimmed into small pieces which are transferred into a stirred dissociation flask. Warm dissociation medium is then added which contains deoxyribonuclease (DNase) and collagenase. The flask is incubated at a temperature of 36-38° C. for 35-45 minutes. After dissociation, the supernatant containing the cells is collected and then filtered into a centrifuge tube. The cells are centrifuged and the cell pellet is re-suspended in HBSS/G. Additional dissociation medium is added to the remaining tumor fragments and the dissociation procedure is repeated for a total of three dissociations. The cells from the three dissociations are pooled in one centrifuge tube and again centrifuged at 2-8° C. The cell pellet is re-suspended in a cryoprotective medium; the volume is based upon the number of viable tumor cells obtained and the desired cell density/vial. A minimum of nine and up to a maximum of 17 vials is prepared for controlled rate freezing. During this freezing cycle, the cell suspension is frozen from +4° C. to −90° C. with a rate of decrease of 1° C./minute until a temperature of −40° C. is reached. This procedure results in the successful cryopreservation of cell viability. The frozen tumor cells are then stored in quarantine under controlled conditions in the vapor phase of liquid nitrogen at a temperature $\leq -110°$ C.

Preparation of the Primary Tumor Cells for Transplantation:

The cryopreserved cells are thawed according to conventional methods. Thawed cryopreserved cells and freshly generated tumor suspensions are kept on ice during the transport into the specific pathogen-free animal facilities. Prior to injection, a sufficient aliquot of suspended cells are harvested and stored for pre- and post-xenograft analysis to ensure genomic and/or antigenic heterogeneity has been preserved through all steps of the process. All vials generated from the tumor are used for injection, and, per vial, cells are drawn through 20 gauge needles into 1.0-10 ml syringes. The 20 gauge needles are replaced with 27-25 gauge needles for injection into immunocompromised mice. Tumor cells may be admixed with Matrigel or similar protein matrix to enhance xenografting take-rates during or after implantation.

Transplantation of Tumor Cells into Immune-Compromised Animals:

Immune-compromised animals (e.g., rats) are kept under specific pathogen-free conditions and are used in accordance with IACUC guidelines. Prior to xenografting, animals are disinfected using 70% ethanol dorsolaterally on both sides of the spine. Per animal, one, two or more 100 µl of tumor suspension are injected subcutaneously into the lateral flank on both sides, approximately 1.5 centimeters apart from each other. Animals are monitored at least once every day.

Intraperitoneal Transplantation of Tumor Cells into Immunocompromised Animals: As an alternative to subcutaneous injection, intraperitoneal injection of tumor cells into immunocompromised animals is also used. Animals are ventrally disinfected using 70% ethanol. Per animal, 1 ml of tumor suspension is injected intraperitoneally. Animals are monitored at least once every day.

Propagation and Harvesting of the Tumor Cells:

After 2-8 weeks, the tumors are large enough to be harvested in accordance with IRB approval and IACUC guidelines, as assessed by tumor volume estimation with caliper measurements. The xenografted animals are sacrificed, submerged in or cleaned with 70% ethanol, and the tumors are removed aseptically and without tumor tissue touching the outside of the animal's skin. Tumors are then assessed for firmness and either teased apart into single cell suspensions by cutting and gently pressing the tissue through a fine mesh or by applying the same dissociation protocol as described above. All tumor cells derived from the same primary tumor are then resuspended in HBSS/G and pooled into one suitable sterile container, mixed gently before sampling, counted, and cell viability assessed by the Trypan Blue exclusion test. The cells are then centrifuged for a final wash using HBSS/G and resuspended in HBSS to reach a final cell concentration of 10% viable cells per ml. A post-xenograft sample is now taken for quality control testing. The suspension is then transferred into sterile cryopreservation vials in 1 ml aliquots and cells are then cryopreserved until further use.

Upon subsequent usage, all tumor cells are used to either prepare a vaccine product containing at least $10^7$ cells per dose or injected into a new set of immune compromised animals and propagated to produce additional tumor cells which are subsequently harvested as described above.

Irradiation:

Vials of propagated and harvested tumor cells are taken from storage and are sterilized and irradiated (200,000 rads)

using a gamma radioactive source to render the tumor cells sterile and non-tumorigenic. One vial is used for quality control testing of the biological product. Eight of the vials comprise four patient doses and are maintained in a separate quarantine area of a liquid nitrogen freezer until the successful completion of all release tests (appearance, tumor cell number and viability, purity, identity, potency, sterility, and endotoxin content). Upon release of the biological product by the qualified person, the patient doses, together with BCG for the first two vaccinations, and all applicable paperwork are shipped to the designated and pre-approved pharmacy or laboratory nearest to the patient for formulation.

Post-Production and Treatment Regimen:

For vaccine preparation, two vials of sterile non-tumorigenic tumor cells and, if necessary, one vial of fresh frozen BCG are taken from storage and packed on dry ice. The vials are accompanied by a vaccine formulation procedure and sent to the pharmacy for compounding. The cells are thawed on a heat block set at 36-38° C. The first two injections have BCG added to the cell suspension. The dose is drawn into a 1 mL syringe, packed on cold blocks, then transported to the physician or nurse for administration to the patient. The expiration of the formulated dose is four hours and begins with the thawing of cells.

The first three vaccinations are administered, by the intradermal route, at weekly intervals, beginning 28 to 35 days after surgery. Each of the first two injections is comprised of thawed irradiated tumor cells ($1.0 \times 10^7 \pm 0.3 \times 10^7$) admixed with BCG ($1.0 \times 10^7$ CFU). The third injection is with irradiated tumor cells, but without BCG. The fourth and final vaccination, also with irradiated tumor cells but without BCG, takes place 6 months after surgery (stage II colon cancer patients) or one month after the completion of chemotherapy (stage III colon cancer patients).

Quality Control Testing:
Tumor Cell Enumeration: Microscopic test for the enumeration of viable tumor cells, non-viable tumor cells, and viable non-tumor cells.
Identity Assay: Fluorescence activated cell sorting (FACS) to determine the presence of adenocarcinoma cells using the tumor-specific human monoclonal antibody 88BV59.
Matrix-Associated Potency and Identity Assays: FACS to count tumor cells that are reactive to EpCAM and CEA, which are tumor-associated antigens.
Purity Assay: FACS to show ≥90% of live cells are tumor cells and/or lymphocytes in the biological product.
Sterility: Test to detect the presence of microbial and fungal contamination in the biological substance and biological product.
Endotoxin Assay: Test to determine the endotoxin level in the biological product.

Example 2

DTH Response Measurements

A phase I/II study (ASI-2002-01) was conducted to evaluate the safety and immunogenicity of the current (non-propagated), sterile, autologous tumor cell vaccines admixed with BCG in patients with stage WM primary adenocarcinoma of the colon. Additionally, this study intended to demonstrate the immune response to the sterile vaccine formulation is equivalent to that of the non-sterile formulation used in previous clinical trials.

To meet the primary endpoint (DTH response measured at 48 hours after the third vaccine, which excluded BCG), a patient was considered to have a positive response to the vaccine if he/she achieved an induration of at least 5 mm. Local, regional, and systemic adverse events were monitored after each vaccine injection and full safety evaluation including physical examination, performance status, complete blood count with differential, blood chemistries, CEA, and urinalysis was conducted 3 and 6 months after surgery and 90 days after the $4^{th}$ vaccination.

All 15 patients treated and evaluated in ASI-2002-01 had an immune response with DTH reactions >5 mm. Moreover, 13 of 15 patients (87%) treated with the sterile vaccine had DTH reactions of at least 10 mm. In the previous trial (8701) which utilized a non-sterile formulation, the vaccine was administered to 128 patients in which 87% experienced a DTH response of at least 10 mm. However, the degree of non-specific erythema was dramatically reduced with the sterile formulation. Erythema is a humoral response, and its reduction presumably reflects the removal of bioburden from the current sterile formulation.

Therefore, the immune response to the sterile vaccine is likely comparable to that of the previous non-sterile product. The results further show that the immunogenic response achieved against this immunization is directed towards tumor-associated antigens and not contamination inherent to the product.

The third and fourth vaccines, which consist of tumor cells alone (no BCG), provide an opportunity to measure DTH. The DTH response is an indicator of the degree of cell-mediated immunity conferred by the initial vaccinations. Two days after vaccine injection, the induration at the site of injection is measured in two perpendicular diameters by the pen method, a standard method for measuring indurations.

Example 3

ONCOVAX® Identity Assay

This Example describes methods for identifying the percentage of CD66 positive tumor cells, after propagation in nude mice, that are also 88BV59 positive by flow cytometry.

Materials And Equipment

MATERIALS: test tube 12×75 mm blue, pipet tip sterile 100 μl with filter, pipet tip sterile 1000 μl with filter, OncoVAX® identity 5EX-lgG antibody, OncoVAX® identity 5EX-88BV59 antibody, OncoVAX® identity CD66-PE antibody, fixation/permeabilization solution kit, HB (1×) without Phenol Red; 500 ml, and purified water EQUIPMENT: Beckman Coulter FC500 flow cytometer, Eppendorf model 5415D centrifuge, refrigerator GKx 7080, digital timer, adjustable volume pipettors.

Procedure:

Sample Preparation

For each specimen a set of two (2) tubes is prepared. The tubes are labeled with IgG3 or 88BV59. The sample to be analyzed is identified (SUB/PRD). The first tube contains human 5-EX IgG3 and anti CD66-PE; the second contains 5-EX 88V59 and anti-CD66-PE. 50 μl of the working dilution of anti-CD66-PE is aliquoted to each tube, followed by 100 μl of well-mixed specimen into each tube. The tube is capped and shaken gently to mix the cells and antibodies, followed by incubation at 15-30° C. for 20-30 minutes. The remaining samples are then stored at 2-8° C.

A 1× solution of Perm/wash buffer is then prepared. For each sample, 0.3 ml of 10× Perm/wash and 2.7 ml purified water are added. The mixture is then capped and mixed by gentle inversion in a centrifuge tube.

First cell wash and permeabolization: 1 ml of HBSS is added to each tube. The tubes are then shaken gently to mix the cells and antibodies, followed by centrifugation for 5-10 minutes at 375-425 g at 15-30° C. The supernatant liquid is then aspirated without disturbing the pellet, and 100 µl of Cytofix/cytoperm solution is added to each tube. The pellet is then resuspended and incubated at 15-30° C. for 20-30 minutes.

Second cell wash and internal stain: The tubes are uncapped and 1 ml of Perm/wash buffer is added to each tube. Tubes are then shaken gently to suspend the cells and centrifuged for 5-10 minutes at 375-425 g and 15-30° C. The supernatant is then aspirated without disturbing the pellet and 50 µl of Perm/wash buffer is added to each tube and shaken gently to resuspend the pellet. The appropriate antibody for internal staining is then added to the respective tubes (100 µ5-EX IgG3 to the IgG3 tube and 100 µl 5-EX 88BV59 to the 88BV59 tube). The tubes are gently shaken to mix the cells and antibodies then incubated at 15-30° C. for 20-30 minutes.

Third cell wash: The tubes are uncapped and 1 ml of Perm/wash buffer is added to each tube. The tubes are capped and shaken gently to suspend the cells which are then centrifuged for 5-10 minutes at 375-425 g at 15-30° C. The tubes are uncapped and supernatant aspirated without disturbing the pellet. Next, 400 µl of HBSS is added to each tube. The tubes are capped and shaken gently to suspend the cells. Tubes are then stored at 2-8° C. until analysis (up to 1 hr).

Tube analysis: Established standard gating parameters for forward and right angle light scatter are used to analyze the cells by FACS. Intact cells are included and dead cells and debris are excluded from the light scatter gate. The 88BV59 tube is used to determine the percent of CD66+ 88BV59+ cells.

Assay validity—Resolution: An observable shift in the fluorescence is noted to distinguish CD66+88BV59+ stained cells from CD66+ IgG3+ control cells.

Percent identity calculation: The percentage of CD66 and 88BV59 positive (CD66+ 88BV59+) tumor cells is divided by the portion which are CD66 positive cells and multiplied by 100 to determine the identity percent.

Using the above procedures, human colon tumor cells harvested after propagation in nude mice would show substantial or complete identity.

Example 4

Potency Assay

This Example describes the methods for identifying and enumerating tumor cells by flow cytometry after propagation in nude mice.

EQUIPMENT: Beckman Coulter FC500 flow cytometer, refrigerator GKx 7080, 2-8° C., timers, adjustable volume pipettors (P200, P1000), and reagent and sample storage.

Samples submitted for analysis would be stored at 2-8° C., then analysis procedures initiated immediately.

Sample Preparation: For each sample three (3) identical replicates are prepared. Each tube contains the OncoVAX® Potency antibody working solution comprised of anti-Ep-CAM FITC, anti-CD6 PE, and anti-CD45 PC5. To each replicate tube, 150 µl of the OncoVAX® Potency antibody working solution is added. To each tube, 100 µl of well-mixed cell sample is added. Cells and antibodies are gently shaken to mix. Any remaining samples are stored at 2-8° C. The tubes are incubated at RT for 2-30 minutes. After incubation, 400 µl of DPBS is added to each tube. The container with flow count fluorospheres (beads) is then vortexed. To each tube, 100 µl of flow count fluorospheres are added. Sample Analysis: Live cells should be included and dead cells and debris should be excluded from the light scatter gate. To obtain the absolute count of tumor and other cells, the amount of beads specified on the Certificate of Analysis provided by the flow count fluorospheres manufacturer are acquired. The percentages and counts of the tumor cells in the tumor region are also acquired. The percentages and counts of the lymphoid cells in the lymphoid region are also acquired.

Calculation of the results: To determine the sample potency (tumor cells/vial), the mean tumor cell count/µl (Region K, Table B) is multiplied by 1000. If necessary, the dilution factor is also used to account for the original concentration during sample preparation. To determine the lymphoid cells/vial, the mean lymphoid cell count/µl (Region Ly, Table B) is multiplied by 1000. If necessary, the dilution factor is also used to account for the original concentration during sample preparation. To calculate the percent recovery, the mean tumor cell count is added to the mean lymphoid cell count and divided by the mean light scatter gate count.

Using the above procedures, human colon tumor cells harvested after propagation in nude mice would show the following potency:

| Test | Specification |
|---|---|
| Tumor cells (Potency) | Live tumor cells: $0.35 \times 10^7$ to $1.3 \times 10^7$ per vial |
| Lymphoid cells | Live Lymphoid cells: $0.13 \times 10^7$ to $1.5 \times 10^7$ per Vial |
| Recovery | ≥80% of Live cell population |

Example 5

Purification of Human Cancer Cells from Expanded Xenograft Material

Following harvest and dissociation of the xenografted tumor(s), the sample may be purified of xenobiotic materials or contaminants, namely live cells or cellular debris associated with the source animal. OncoVAX® is an autologous vaccine and by definition the circulating cells, tumor-associated stroma, and any other cellular debris which may act as a contaminant in the vaccine are still considered "self" by the immune system. However, during the xenograft process, human cancer cells are supported by mouse-derived stroma and vasculature. As these constitute foreign material to the original patient, these contaminants represent a greater risk for adverse events than self-derived tissue. Thus, following xenograft expansion, cross-species reactivity to biological material may be minimized to reduce the risk of potential hypersensitivity reactions and drug-induced allergies. Once the cells have been dissociated into a single-cell suspension, the mixture is treated with magnetic or non-magnetic beads conjugated to monoclonal antibodies specific for mouse biological markers (including, but not limited to, mouse-specific anti-CD44 and/or anti-CD55) or general antigenic markers for endothelial or hematopoietic cells of origin. After binding mouse cells within the suspension, the sample is centrifuged, enriching for human tumor cells by negative selection. The purity of the separation is then quantified in an OncoVAX® identity assay and the resulting genomic fingerprint is tested against a homogenous sample of the original tumor dissociation.

Example 6

Characterization of Human Cancer Cells Following Xenograft Expansion

The clinical efficacy of vaccine products in accordance with the present disclosure OncoVAX® lies in its ability to embrace and exploit tumor heterogeneity. Any attempt to augment its source material that results in a fundamental change in the unique antigenic profile associated with the individual patient increases the of treatment failure. Consequently, a representative suspension of cells from the original tumor (pre-xenografting) and the tumor implant after enriching for human cells (post-xenografting) may be compared to ensure immunogenic continuity throughout the expansion process. Various screening methods can be utilized to achieve this quality control including, but not limited to, comparative genomic hybridization, chromosome karyotyping, single nucleotide polymorphism (SNP) analysis, short-tandem repeat profiling, transcriptomic (RNA-seq) or genomic deep sequencing, RNA microarray analysis, or flow cytometric analysis. Significant alterations in the chromosomal, mutational, or gene expression profile of the tumor cells post-xenografting represents a failure to preserve patient-specific heterogeneity. Accordingly, following RNA microarray analysis of a homogenous sample of the primary tumor cells and a homogenous sample of the xenograft-propagated tumor cells, the xenograft cells would exhibit significant homology, preferably at least 85% sequence homology, to the cells of the primary tumor.

The present invention thus embraces the heterogeneity of tumor antigens, via autologous cancer vaccines, and extends this technology to cancers, including solid tumors whose relatively small size would otherwise make them too small for effective use as primary tumors for the manufacture of autologous vaccine products and associated methods of treatment.

The manufacturing processes include transplanting and propagating patient tumor cells in immune-compromised animals and harvesting the propagated cells from the animals to prepare vaccine compositions of sufficient quantity, which have the biological, phenotypic, antigenic and immunogenic properties of the primary tumor. The invention also provides autologous vaccine products and compositions containing a greater number of viable tumor cells than the patient's primary tumor, wherein the tumor cells of the vaccine have at least 85% sequence homology to the cells of the primary tumor, and provides methods for eliciting an immune response to prevent the recurrence of metastases by eliminating minimal residual disease in the individual, specific cancer patient, through the administration of a uniform mixture of heterogeneous cell product, and/or a xenograft-expanded, viable, sterile, non-tumorigenic but immunogenic cells, in a dose and a regimen sufficient to elicit an immune response to prevent micromestasteses and/or the recurrence of malignant disease.

While several of the above Examples relate to colon cancer, the present invention is not limited thereto and is only limited by the scope of the appended claims.

What is claimed is:

1. A method for making an injectable autologous, anti-neoplastic vaccine containing at least $10^7$ viable, non-tumorigenic tumor cells, comprising: excising a solid tumor from a cancer patient to obtain at least 95% of the patient's solid tumor tissue, wherein the excised tumor tissue has a weight of less than 3.5 grams; digesting the excised tumor tissue to obtain dissociated tumor cells; transplanting the excised tumor cells into an immune-compromised animal; propagating the tumor cells in the animal to obtain expanded tumor tissue; harvesting the expanded tumor tissue from the animal to obtain harvested tumor cells, wherein the harvested tumor tissue has a weight of at least 3.5 grams; applying a dose of gamma radiation to the harvested tumor cells to render the cells non-tumorigenic; combining the non-tumorigenic tumor cells with a pharmaceutically acceptable carrier for injection to prepare an injectable dose for the patient containing at least $10^7$ tumor cells; and injecting the injectable dose into the patient for eliciting an immune response to prevent recurrence of metastases, wherein the patient is human patient.

2. A method according to claim 1, wherein the expanded cells have at least 85% sequence homology to the tumor cells of the patient's solid tumor.

3. A method according to claim 1, further digesting the excised tumor tissue with an enzyme to obtain dissociated tumor cells and mixing the dissociated tumor cells to form a homogeneous suspension.

4. A method according to claim 1, further comprising digesting the harvested tumor tissue to obtain dissociated harvested tumor cells and mixing the dissociated harvested tumor cells to form a homogeneous suspension.

5. A method according to claim 1, wherein the tumor cells transplanted into the animal comprise 95-100% by weight of the patient's solid tumor.

6. A method according to claim 1, further comprising transplanting the harvested tumor tissue into a second immune-compromised animal, propagating the tumor tissue in the second animal, and harvesting the propagated tumor tissue from the second animal to prepare the injectable dose containing at least $10^7$ tumor cells.

7. A method according to claim 1, where the animal is a rat or an athymic nude mouse which has received treatment to reduce Natural Killer Cell activity or has Severe Combined Immunodeficiency Disease (SCID).

8. A method according to claim 1, where the transplanted tissue is harvested when it has a weight of 3.5 to 4 g.

9. The method of claim 1, further comprising treatment of the harvested tumor, before dissociation, with a disinfectant solution at a concentration and for a duration that provides antimicrobial activity while minimizing cytotoxicity.

10. The method of claim 1, further comprising characterizing the antigenic profile of the harvested cells via RNA sequencing to ensure that heterogeneity to the patient's tumor has been preserved.

11. The method of claim 1, further comprising applying a dose of gamma radiation to the harvested cells in an amount sufficient to inactivate microorganisms and tumorigenicity and preserve the viability of the cells, to obtain sterile, non-tumorigenic and immunogenic tumor cells.

* * * * *